United States Patent [19]
Sucholeiki

[11] Patent Number: 5,693,720
[45] Date of Patent: Dec. 2, 1997

[54] SOLID-PHASE SYNTHESIS UTILIZING PHOTOCHEMICAL CARBON-SULFUR BOND CLEAVAGE OF THIOETHERS

[75] Inventor: Irving Sucholeiki, Watertown, Mass.

[73] Assignee: Eli Lilly and Company, Indianapolis, Ind.

[21] Appl. No.: 458,325

[22] Filed: Jun. 2, 1995

Related U.S. Application Data

[62] Division of Ser. No. 215,607, Mar. 22, 1994, Pat. No. 5,502,246.
[51] Int. Cl.$^6$ ............................................. C08F 8/34
[52] U.S. Cl. ................. 525/333.5; 525/349; 525/350; 525/351; 562/426; 529/329.4
[58] Field of Search .................... 525/333.5, 349, 525/350, 351; 562/426

[56] References Cited

U.S. PATENT DOCUMENTS

| | | | |
|---|---|---|---|
| 4,258,193 | 3/1981 | Fujii et al. | 546/281 |
| 5,061,509 | 10/1991 | Naito et al. | 427/13 |
| 5,143,854 | 9/1992 | Pirrung et al. | 436/518 |
| 5,276,140 | 1/1994 | Nitecki et al. | 530/391.1 |
| 5,349,066 | 9/1994 | Kaneko et al. | 546/294 |

*Primary Examiner*—C. Warren Ivy
*Assistant Examiner*—Sreeni Padmanabhan
*Attorney, Agent, or Firm*—Roger S. Benjamin; David E. Boone; Daniel W. Collins

[57] ABSTRACT

A method for photochemical cleavage of carbon-sulfur bonds in conjunction with solid-phase synthesis utilizing a deoxygenated solvent and light to cleave the carbon-sulfur bond from a heterogeneous support. Also disclosed are compounds for use with said photochemical cleavage and methods of preparing them.

3 Claims, No Drawings

SOLID-PHASE SYNTHESIS UTILIZING PHOTOCHEMICAL CARBON-SULFUR BOND CLEAVAGE OF THIOETHERS

This application is a division of application Ser. No. 08/215,607 filed Mar. 22, 1994, now U.S. Pat. No. 5,502,246.

FIELD OF THE INVENTION

The invention relates to a method for preparing non-peptide compounds utilizing solid-phase synthesis. More particularly, it relates to a method for performing solid phase chemistry wherein the product compounds are released from the solid support by photochemically breaking a carbon-sulfur bond.

BACKGROUND OF THE INVENTION

Recently, there has been a flurry of interest in what is termed a "molecular diversity" approach to finding new drug entities wherein organic synthesis is used to generate libraries of organic peptide and non-peptide compounds by incorporating a series of "building blocks," usually on a solid support utilizing the process known as solid-phase synthesis. Such libraries may be generated by covalently anchoring an organic compound which serves as a building block to a solid support such as a polymeric resin, silica, glass, cotton or cellulose; adding functional groups or other compounds onto the first compound; and cleaving the finished product from the solid support when the synthesis is complete. The compound may be attached to the solid support by means of a "linker." A linker can be any group that holds the starting material onto the solid support (or a molecule containing such a group), which is stable to the reaction conditions necessary to complete the synthesis and is easily cleavable upon completion of the synthesis. While there has been a growing evolution in the design of compounds to be used as building blocks for such libraries, there still remains a heavy reliance on ester and amide functionality for attaching the compounds to the support. While this may be suitable in some specific cases, it fails as a general strategy for the production of a library that incorporates only those functionalities necessary for biological activity. Those compounds that retain the vestiges of the amide linker may also be susceptible to hydrolysis by in vivo exopeptidases. This invariably would complicate the analysis for determining the essential active components in a drug lead. Finally, linkers that rely on ester or amide functionality, in many cases, require harsh cleavage conditions such as trifluoroacetic acid as part of their cleavage protocol. The total removal of trifluoroacetic acid, for example, typically requires one to incorporate in the cleavage protocol a series of ether precipitation steps. Such steps make automation difficult.

Since the early 1960s there has been a large amount of work done on photoactive protecting groups that, upon irradiation in solution, release the active groups. For example, it is known that one can make a Friedel-Crafts acylation of polystyrene to give an alpha bromo ketone that can be treated with a free carboxylic acid to give the resulting ester on the support. When this support is irradiated with 350 nm light, the carbon-oxygen bond breaks, regenerating the carboxylic acid [S. Wang, *J. Org. Chem.*, (1976), 41: 3258].

This method was later improved upon by making a linker that incorporates the alpha bromo ketone and which can be attached to any support containing a free amine or alcohol. When irradiated with 350 nm light, the carbon-oxygen bond breaks, releasing the carboxylic acid from the support [F. S. Tjoeng et al., *Tetrahedron Lett.*, (1982), 23: 4439]. It was originally believed that this method of synthesis produced only one isomer of the linker, but it was later discovered that three structural isomers of the linker had been produced [F. Uggieri et al., *J. Org. Chem.* (1986), 51: 97].

It is also known that a carbon-nitrogen bond can be cleaved upon irradiation with 350 nm light. Upon irradiation, C-terminal N-methylated peptide amides may be isolated [V. N. Pillai et al., *Indian J. of Chemistry*, (1988), 27B: 1004]. However, a method for the photolytic cleavage of a carbon-sulfur (C—S) bond from a heterogeneous support has not yet been developed.

Thus there remains a need for the preparation of novel linkers and methods of cleaving the product compounds from solid supports that contain no vestigial functional groups such as carboxylic acid or an amide bond, and form a single pure isomer. Furthermore, such compounds and methods should be useful under conditions that can be easily automated, and in combination with commercially available supports allowing for in-situ cleavage and biological testing of scaffolds in an aqueous solvent.

SUMMARY OF THE INVENTION

The present invention is directed to a method for photochemical cleavage of a carbon-sulfur (C—S) bond in conjunction with solid-phase synthesis, and compounds utilized in said method. The invention represents an advance in solid-phase chemistry useful in preparing organic non-peptide compounds for use in creating molecular diversity libraries.

In one embodiment, the invention involves a linker compound used to link a compound to a solid support for the purpose of solid-phase synthesis by means of a C—S bond, which can then be photochemically cleaved to free the compound from the solid support. A preferred linker compound has the following formula:

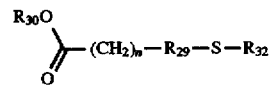

wherein:

$R_{29}$ is selected from the group consisting of $C_{0-4}$ alkyl, phenyl and

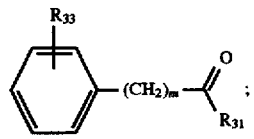

$R_{30}$ is selected from the group consisting of H and $C_{1-4}$ alkyl;

$R_{31}$ and $R_{34}$ is selected from the group consisting of $C_{1-4}$ alkyl and phenyl;

$R_{32}$ is selected from the group consisting of H, t-butyl,

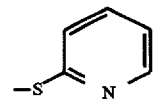

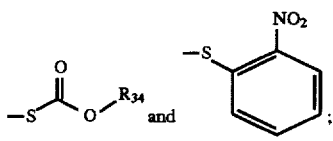

$R_{33}$ is selected from the group consisting of H and up to three $C_{1-4}$ alkoxy substitutents;

n is 1 to 10; and m is 0 to 10.

A particularly preferred linker compound has the following formula:

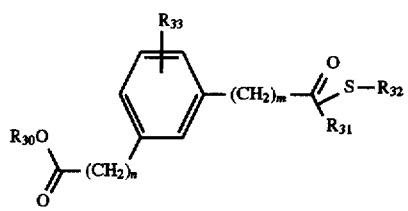

Formula I wherein:

$R_{30}$ is selected from the group consisting of H and $C_{1-4}$ alkyl;

$R_{31}$ and $R_{34}$ are selected from the group consisting of $C_{1-4}$ alkyl;

$R_{32}$ is selected from the group consisting of H, t-butyl,

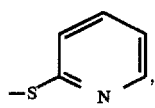

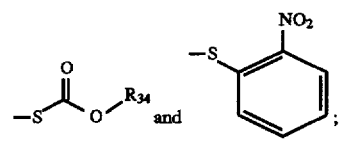

$R_{33}$ is selected from the group consisting of H and up to three $C_{1-4}$ alkoxy substituents;

n is 1 to 10; and m is 0 to 10.

In another embodiment, the invention involves the combination of the linker and an amine, halide, or alcohol functional group-containing solid support, and a method for preparing said combination. A preferred coupled linker has the following formula:

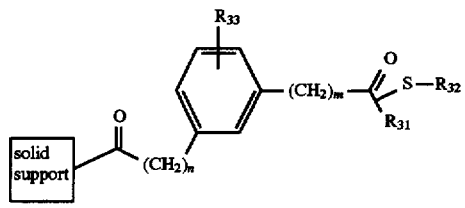

Formula II wherein:

$R_{31}$ and $R_{34}$ are selected from the group consisting of $C_{1-4}$ alkyl;

$R_{32}$ is selected from the group consisting of H, t-butyl,

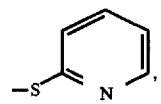

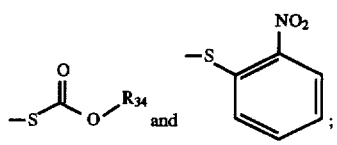

$R_{33}$ is selected from the group consisting of H and up to three $C_{1-4}$ alkoxy substituents;

n is 1 to 10; and m is 0 to 10.

In a further embodiment, the invention involves the combination of an organic compound, the linker and an amine-containing solid support, and a method for preparing said combination. In a preferred embodiment, this structure has the following formula:

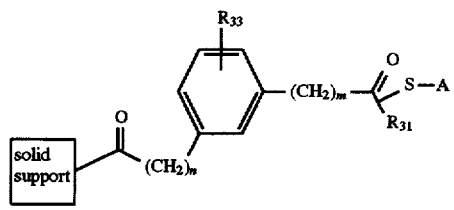

wherein:

A is an organic non-peptide compound;

$R_{31}$ is selected from the group consisting of $C_{1-4}$ alkyl;

$R_{33}$ is selected from the group consisting of H and up to three $C_{1-4}$ alkoxy substitutents;

n is 1 to 10; and m is 0 to 10.

In still another embodiment, the invention involves a method for solid-phase synthesis utilizing photochemical cleavage of the C—S bond linking an organic compound to a solid support. Preferably the method for solid-phase synthesis of compounds utilizing photochemical cleavage of the C—S bond comprises the steps of preparing a linker molecule; attaching said linker molecule to an amine, halide, or alcohol functional group-containing solid support; attaching an organic non-peptide compound to the linker via a C—S bond; and cleaving the C—S bond utilizing UV light and a deoxygenated solvent to separate said compound from said linker.

Preferred embodiments involve the use of a linker known in its protected form as 3-[2-[(2-nitrophenyl)dithio] propionyl]-6-methoxyphenylacetic acid (NpSSMpact). This linker is unique because of its ability to carry a protected thiol in the form of a disulfide and because its rate of photolytic cleavage is much faster than a simple alkyl linker.

Any commercially available peptide synthesis support containing an amine, halide or alcohol functional group may be used. Preferred embodiments involve the use of polystyrene, acrylamide, polyethylene glycol (PEG), polystyrene acrylamide, polyethylene glycol-polystyrene (PEG-PS) resin or silica as the solid support.

DETAILED DESCRIPTION OF THE INVENTION

The technology of the present invention presents for the first time the solid-phase photochemical cleavage of a C—S bond used to link an organic compound to a solid support, thereby overcoming many of the disadvantages of using ester or amide functionalities as linkers. Furthermore, the compounds of this invention present many advantages over existing cleavage methods. The cleaved product contains no vestigial functional groups such as a carboxylic acid or an amide bond. The deprotection conditions involve only solvent and light, conditions that make the transfer of this technology to automation extremely easy. In addition, this technology can be used with any solid support presently used in synthetic reactions. Examples of suitable commercially available supports include polyethylene glycol-polystyrene (PEG-PS) resin, polystyrene resin, acrylamide resin, polyethylene glycol resin, polystyrene-acrylamide resin and silica. These supports combined with this new photochemical technology allows the in-situ cleavage and biological testing of scaffolds in an aqueous solvent.

The present invention involves the solid-phase photochemical cleavage of a C—S bond to give either the resulting disulfide 3 or the toluel derivative 4 of the scaffold as shown in Scheme I wherein a and b represent the cleavage sites. The wavelength of the light can be between 10 and 700 nm, preferably is between 300 and 400 nm, and most preferably is 350 nm.

Scheme 1

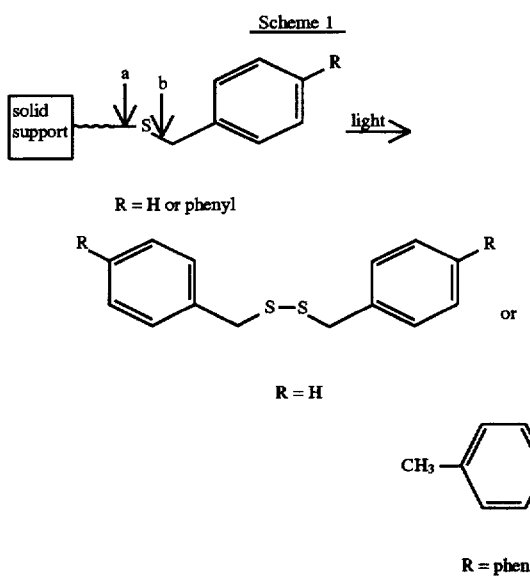

R = H or phenyl

R = H

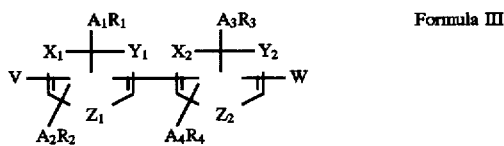

R = phenyl

Suitable organic compounds for use as building blocks in the present invention include compounds of the following Formulas III through VI:

Formula III

wherein:

$X_1$, $Y_1$, $Z_1$ are any accessible combination of CH, CHCH, O, S, N provided that at least one is CH or CHCH and not more than one is CHCH;

$X_2$, $Y_2$, $Z_2$ are any accessible combination of CH, CHCH, O, S, N provided that at least one is CH or CHCH and not more than one is CHCH;

W is H or

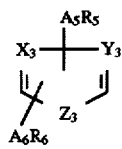

$X_3$, $Y_3$ and $Z_3$ are any accessible combination of CH, CHCH, O, S, N provided that at least one is CH or CHCH and not more than one is CHCH;

V is H, $C_{1-6}$ alkyl, halo, OH, $CO_2H$, $CH_2SH$, or $NR_{22}R_{23}$;

$A_1$, $A_2$, $A_3$, $A_4$, $A_5$, and $A_6$ independently are absent or present as O, S, $NR_{60}$ or $C_{0-6}$ alkylC(O)$NR_{21}$, provided that at least three are present;

$R_1$, $R_2$, $R_3$, $R_4$, $R_5$, and $R_6$ independently are H, $C_{1-6}$ alkyl, $C_{1-6}$ alkylCO$_2R_{15}$, $C_{1-6}$ alkyl$R_{16}R_{17}$, $C_{1-6}$ alkylOR$_{24}$, $C_{1-6}$ alkyl$NR_{25}R_{26}$, $C_{1-6}$alkylNHC(NH)NH$_2$, or $C_{1-6}$alkyl-D;

D is any saturated or unsaturated five or six membered cyclic hydrocarbon or heterocyclic ring system containing one or two O, N, or S atoms that is substituted by any accessible combination of 1 to 4 substituents selected from halogen, $CF_3$, $C_{1-6}$ alkyl, $NR_7R_8$, $OR_9$, $SR_{10}$, or $COR_{11}$;

$R_7$, $R_8$, $R_9$, $R_{10}$, $R_{12}$, $R_{13}$, $R_{14}$, $R_{20}$, $R_{21}$, $R_{22}$, $R_{23}$, and $R_{60}$ independently are H or $C_{1-6}$ alkyl;

$R_{16}$, $R_{17}$, $R_{18}$, $R_{19}$, $R_{24}$, $R_{25}$, and $R_{26}$ independently are H, $C_{1-6}$ alkyl, phenyl, or substituted phenyl;

$R_{11}$ is $OR_{12}$ or $NR_{13}R_{14}$; and
$R_{15}$ is $OR_{18}$ or $NR_{19}R_{20}$.

Formula IV

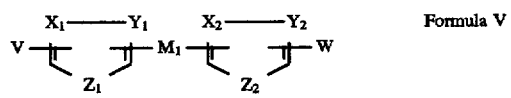

wherein:

X, Y, and Z may reside at any allowed position about the ring and are any accessible combination of CR, N, NR, O and S;

R is H or $C_{1-4}$alkyl; and
n' is 1 or 2.

Formula V

wherein:

$M_1$ and $M_2$ independently are O, OCO, CO, $CO_2$, O($C_{1-4}$alkyl), ($C_{1-4}$alkyl)O;

$X_1$, $Y_1$ and $Z_1$ are any accessible combination of CH, CHCH, O, S, N, and NH provided that at least one is CH or CHCH and not more than one is CHCH;

$X_2$, $Y_2$ and $Z_2$ are any accessible combination of CH, CHCH, O, S, N, and NH provided that at least one is CH or CHCH and not more than one is CHCH;

W is H or

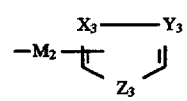

V is H, $C_{1-6}$alkyl, halo, OH, $CO_2H$, $CH_2SH$, $NR_{22}R_{23}$, $CH_2$halo, $CH_2R_{75}$, $CH_2CO_2R_{76}$, or $CH_2NR_{77}R_{78}$;

$X_3$, $Y_3$ and $Z_3$ are any accessible combination of CH, CHCH, O, S, N, and NH provided that at least one is CH or CHCH and not more than one is CHCH; and $R_{22}$, $R_{23}$, $R_{75}$, $R_{76}$, $R_{77}$, and $R_{78}$ independently are H or $C_{1-6}$alkyl.

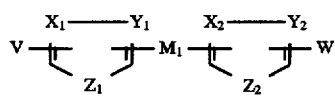  Formula VI wherein:

$X_1$, $Y_1$ and $Z_1$ are any accessible combination of CH, CHCH, O, S, N, and NH provided that at least one is CH or CHCH and not more than one is CHCH;

$X_2$, $Y_2$ and $Z_2$ are any accessible combination of CH, CHCH, O, S, N, and NH provided that at least one is CH or CHCH and not more than one is CHCH;

W is H or

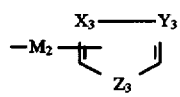

$M_1$ and $M_2$ independently are $CONR_{70}$, $NR_{70}CO$, $OCONR_{71}$, $NR_{71}COO$, $(C_{0-3}alkyl)NR_{72}$, $NR_{72}(C_{0-3}alkyl)$, $NR_{80}CONR_{81}$;

V is H, $C_{1-6}$alkyl, halo, $(C_{0-4}alkyl)OH$, $(C_{1-4}alkyl)SH$, $(C_{0-4}alkyl)NR_{22}R_{23}$, or $(C_{0-4}$ $alkyl)CO_2R_{76}$;

$X_3$, $Y_3$ and $Z_3$ are any accessible combination of CH, CHCH, O, S, N, and NH provided that at least one is CH or CHCH and not more than one is CHCH; and $R_{22}$, $R_{23}$, $R_{70}$, $R_{76}$, $R_{71}$, $R_{72}$, $R_{80}$, and $R_{81}$ independently are H or $C_{1-6}$alkyl.

The photosensitive linker that allows one to attach a compound and later cleave it from the support is a mercapto-substituted carboxylic acid or ester which is protected as the disulfide, as shown in the formula below:

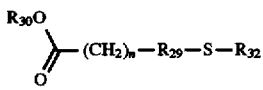

wherein:

$R_{29}$ is selected from the group consisting of $C_{0-4}$ alkyl, phenyl and

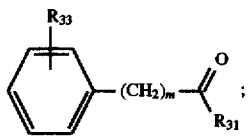

$R_{30}$ is selected from the group consisting of H and $C_{1-4}$ alkyl;

$R_{31}$ and $R_{34}$ is selected from the group consisting of $C_{1-4}$ alkyl and phenyl;

$R_{32}$ is selected from the group consisting of H, t-butyl,

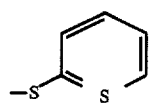

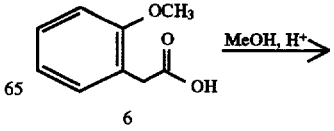

$R_{33}$ is selected from the group consisting of H and up to three $C_{1-4}$ alkoxy substitutents;

n is 1 to 10; and m is 0 to 10.

The linker is preferably the mercapto-substituted phenyl ketone of Formula I:

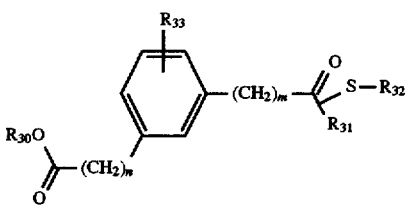  Formula I wherein:

$R_{30}$ is selected from the group consisting of H and $C_{1-4}$ alkyl;

$R_{31}$ and $R_{34}$ are selected from the group consisting of $C_{1-4}$ alkyl;

$R_{32}$ is selected from the group consisting of H, t-butyl,

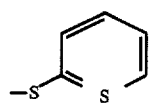

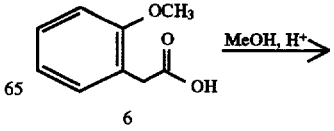

$R_{33}$ is selected from the group consisting of H and up to three $C_{1-4}$ alkoxy substituents;

n is 1 to 10; and m is 0 to 10.

The protected linker is most preferably 3-[2-[(2-nitrophenyl)dithio]propionyl]-6-methoxyphenylacetic acid (NpSSMpact) or its precursor, 3-[(2-chloro)propionyl]-6-methoxyphenylacetic acid (chloroMpact). As used throughout this specification and claims, the term NpSS means (2-nitrophenyl)dithio. The synthesis of the NpSSMpact linker 5 begins with treatment of 2-methoxyphenylacetic acid (6) with methanol and sulfuric acid to give the corresponding phenylacetate 7 (Scheme II). Alternatively, the 2-methoxyphenylacetic acid can be treated with 2 equivalents of boron trifluoride and methanol and refluxed for two hours.

Scheme II

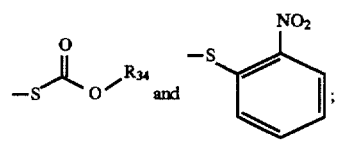

Scheme II -continued

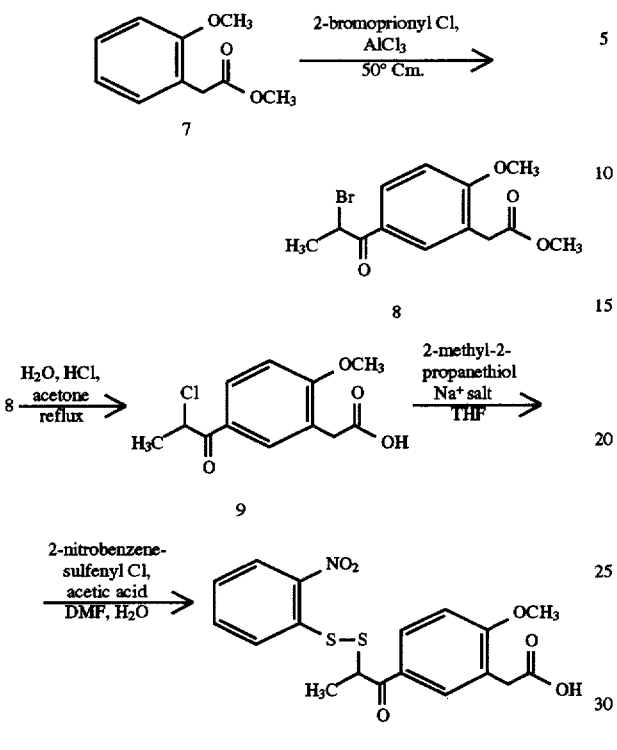

The phenyl acetate is then treated with 2-bromopropionyl chloride in the presence of aluminum or ferric trichloride to give the corresponding Friedel-Crafts acylation product 8. The phenylacetate 8 is then refluxed in acetone and aqueous HCl to give the alpha-chloro derivative chloroMPact 9. The chloroMPact linker 9 may then be treated with the sodium salt of 2-methyl-2-propanethiol in tetrahydrofuran (THF) distilled from Na/benzophenone to give the corresponding thioether which is then treated without any further purification with 2-nitrobenzenesulfonyl chloride to give the NpSSMpact linker 5.

Both the NpSSMpact linker 5 and its precursor (chloroMpact linker) 9 were coupled to an amine-containing solid support, such as polyethylene glycol-polystyrene resin (for example, TentaGel™ resin having a substitution of 0.29 mmole/g, from Novabiochem) support using standard diisopropylcarbodiimide (DIC) coupling methods (Scheme IIIa) [see for example E. Bayer et al., *Chemistry of Peptides and Proteins* (1986) 3: 3]. As a comparison support 10 was coupled with the biphenyl acid compound 15 to give the biphenylether support 16 (Scheme IIIb).

Scheme III

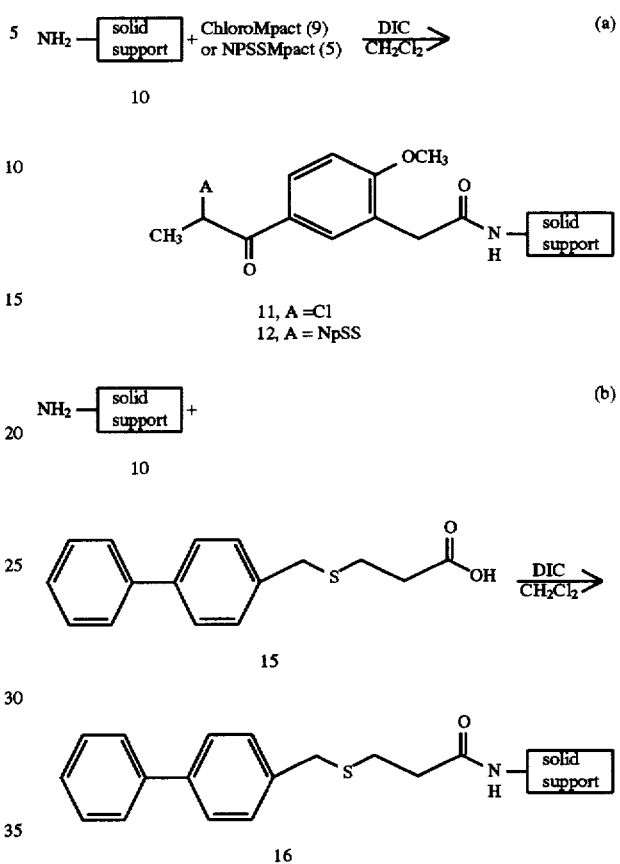

The substitution of support 11 was determined by quantitative ninhydrin of the free amines remaining after amide formation [V. K. Sarin et al., *Anal. Biochem.* (1981) 117: 147]. The substitution of support 12 was determined using a modified Ellman-type assay for free thiol [I. Sucholeiki et al., *J. Org. Chem.* (1993) 58: 1318]. Support 11 was treated with benzyl mercaptan and diisopropylethylamine ((DIEA) distilled from ninhydrin under reduced pressure) to give the resulting benzylthioether derivative 13. Support 12 was first treated with β-mercaptoethanol (BME) and DIEA to give the free thio form of the linker HSMpact), which was then subsequently alkylated with 4-phenylbenzyl bromide to give the resulting biphenylthioether adduct 14 (Scheme IV).

Scheme IV

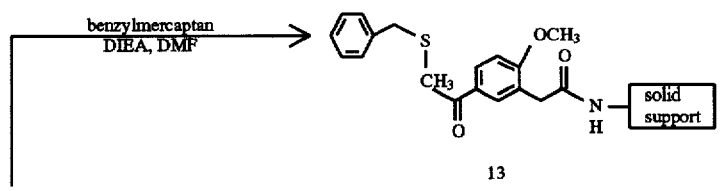

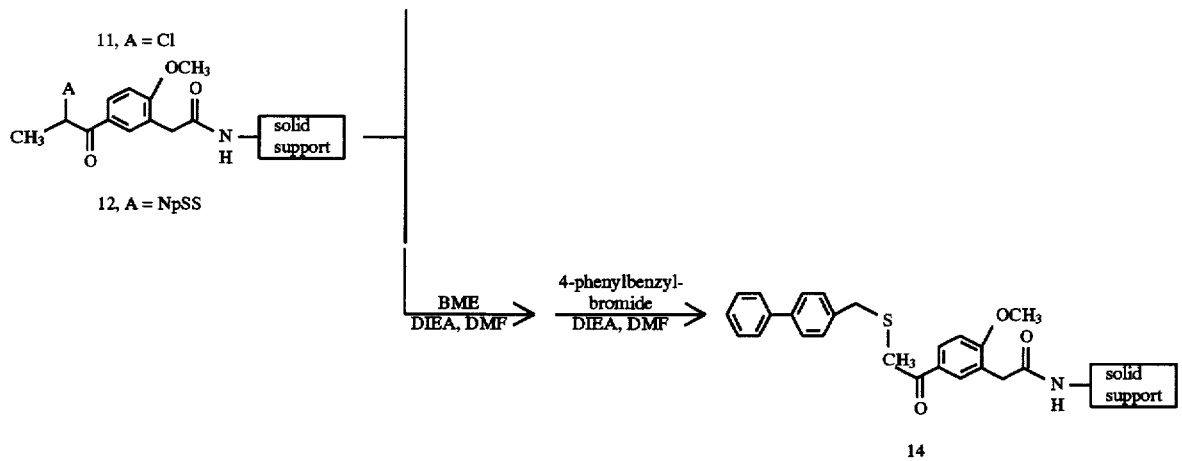

To cleave the C—S bond, to each support was then added acetonitrile (HPLC-grade, obtained from EM Science), which in some cases was de-oxygenated by a known freeze-thaw method. The reaction mixtures were then irradiated at 350 nm, under a nitrogen atmosphere. While not being limited to a particular reaction procedure, a preferred method involves using a Rayonet photochemical reactor in combination with quartz reaction vessels. The products were then analyzed using reverse-phase HPLC, GC mass spectrometry and $^1$H NMR spectroscopy. In some cases the products were isolated and completely characterized. The results of these photochemical studies can be seen in Table I.

TABLE I[a]

| Linker | R | Solvent Conditions/Rxn Time | % 3 | % 4 | % 1 |
|---|---|---|---|---|---|
| —CH$_2$CH$_2$— | phenyl | non-deoxygenated/1.5 h | 0 | 15 | 8 |
|  | phenyl | deoxygenated/2 h, 17 min | 0 | 69 | 3 |
|  | phenyl | deoxygenated/5 h | 0 | 75 | 2 |
| (substituted aryl linker) | H | deoxygenated/2 h, 30 min | 100 | 0 |  |
|  | phenyl | deoxygenated/2 h | 0 | 95 |  |
|  | phenyl | deoxygenated/5 h | 0 | 94 |  |

[a]% ratios were determined using $^1$H NMR integration

Irradiation of the β-keto-sulfide 13 (R=H), produces the literature-precedented disulfide 3. Conversely, irradiation of resin 14 (R=phenyl), gives one exclusively biphenyl compounds 17 and 4 (Table I). When one compares the resin containing the Mpact linker (14) versus the more simple 3-mercaptopropionic acid linker (16), one finds that the ratio of aldehyde (17) to methyl biphenyl (4) is much lower in the former. The rate of production of biphenyl 4 is also much faster in the resin containing the Mpact linker (14), versus the one containing the 3-mercaptopropionic acid group.

The following examples illustrate but do not limit the scope of the invention disclosed in this specification. All percentages are by weight percent unless otherwise indicated.

EXAMPLE 1

Preparation of 2-Methoxymethyl phenylacetate (7).

To a 100 mL round bottom flask was added 10.2 grams (61.3 mmole) of 2-methoxyphenylacetate, 70 mL of anhydrous methanol and 1.5 mL of concentrated sulfuric acid and the resulting mixture refluxed for 17 hours. After 17 hours, the solvent was removed under reduced pressure to give an oil. The oil was dissolved in 100 mL of diethyl ether and organic washed with 150 mL of saturated $NaHCO_3$ solution, dried over $MgSO_4$, filtered and volatile components removed under reduced pressure to give 9.26 grams (83% yield) of 7 as a light tan oil.

EXAMPLE 2

Preparation of Methyl [3-(2-bromopropionyl)-6-methoxyphenyl]acetate (8).

To a 150 mL round bottom flask was added 15 grams (112 mmole) of $AlCl_3$ and the solid placed under vacuum, then under nitrogen atmosphere. To the solid was then added 50 ml of tetrachlorethane and 5.7 mL (56.5 mmole) of 2-bromopropionyl chloride and the mixture was heated at 45° C. for 20 minutes. To the reaction mixture was then added 10.0 grams (55.0 mmole) of 2-methoxy phenylacetate (7) dissolved in 6 mL of tetrachlorethane over a period of 25 minutes, making sure that the temperature of the reaction mixture did not exceed 50° C. After addition, the reaction was allowed to stir at 50° C. for 5 hours. After 5 hours the reaction mixture was allowed to sit at room temperature for 10 hours. After 10 hours, the reaction mixture was poured into a 250 mL beaker containing 150 mL of packed ice. To the aqueous mixture was then added 0.5 mL of concentrated HCl and then poured into a 250 mL separatory funnel and 50 ml of $CH_2Cl_2$ was then added. The organic was then separated and the aqueous layer extracted with another 50 mL of $CH_2Cl_2$ and then organics combined and washed with 200 mL of 10% NaOH solution, 200 mL $H_2O$ and then the organic layer was separated. The organic layer was then dried over $MgSO_4$, filtered and the volatile components removed under reduced pressure at 50°–60° C. to give a dark purple-red oil which was purified by flash chromatography ($SiO_2$, 5×15 cm column) first with 50% hexane-$CH_2Cl_2$ then with $CH_2Cl_2$ to isolate 11.6 grams (66% yield) of 8 as a thick oil.

EXAMPLE 3

Preparation of 3-[(2-Chloro)propionyl]-6-methoxyphenyl acetic acid (9).

To a 250 mL round bottom flask containing 11.4 grams (36.3 mmole) of methyl ester 8 was added 70 mL of acetone and the mixture sonicated until solution was complete. To the solution was then added 15 mL of concentrated HCl, 20 mL of $H_2O$ and the resulting solution refluxed for 6 hours. At the end of 6 hours the volatile components of the reaction mixture were removed under reduced pressure to give an oil/water mixture which was then dissolved in 100 mL of $CH_2Cl_2$. The organic/aqueous mixture was then extracted with 150 mL of saturated $NaHCO_3$. The aqueous layer was then removed and acidified with concentrated hydrochloric acid to a pH equal to 1. The aqueous mixture was then quickly extracted with 100 mL of $CH_2Cl_2$. The organic layer was then dried over $MgSO_4$, filtered and the volatile components removed under reduced pressure to give an oil which crystallized to give 6.0 grams (64% yield) of 9 as a white solid.

EXAMPLE 4

Preparation of 3-[2-[(2-Nitrophenyl)dithio]propionyl]-6-methoxyphenylacetic acid (5).

To a 50 mL round bottom flask containing 0.9 grams (8.82 mmole) of the sodium salt of 2-methyl-2-propanethiol was added 0.25 grams of sodium hydride (11.3 mmole) and the resulting mixture placed under vacuum and then under a nitrogen atmosphere. To the mixture was then added 15 mL of anhydrous tetrahydrofuran and the mixture cooled to 0° C. To the cooled mixture was added 1.5 grams (5.84 mmole) of 9 dissolved in 15 mL of anhydrous THF over a period of 10 minutes. After addition, the reaction mixture was allowed to stir, at room temperature and under a nitrogen atmosphere for 18 hours. After 18 hours the volatile components of the reaction mixture were removed under reduced pressure to give a brown solid. The brown solid was dissolved in 80 mL of $H_2O$ and aqueous washed with 100 mL of diethyl ether. The aqueous layer was then acidified with 1 mL of concentrated HCl (pH=1) and then extracted (2×100 mL) with diethyl ether and organic layers combined, dried over $MgSO_4$, filtered and volatile components removed under reduced pressure to give 1.75 grams of the t-butyl thioether product which was used without any further purification.

To a 25 mL round bottom flask containing 1.75 grams (5.64 mmole) of the crude t-butyl thioether was added 2 mL of dimethyl formamide, 4 mL of concentrated acetic acid and 1 mL of $H_2O$ and mixture sonicated until the solution was complete. To the solution was then added 1.6 grams (8.44 mmole) of 2-nitrobenzenesulfenyl chloride and mixture stirred, in the dark, for 24 hours. After 24 hours, the volatile components of the reaction mixture were removed under reduced pressure to give an oil/water mixture. To the mixture was then added 15 mL of $H_2O$, cooled to freezing and then lyophilized overnight. After lyophilization, the remaining solid was taken up in $CH_2Cl_2$ and purified by flash chromatography ($SiO_2$, 3.5×17 cm column) first with $CH_2Cl_2$, then with 50% diethyl ether-$CH_2Cl_2$ and then with 10% methanol-$CH_2Cl_2$ to isolate a yellow oil which crystallized upon standing to give 1.41 grams (59% yield) of 5 as a yellow crystalline solid.

EXAMPLE 5

Coupling of ChloroMpact to TentaGel to give ChloroMpact-PEG-PS (11).

To a peptide synthesis vessel was added 3.0 grams of TentaGel 10 (0.87 mmole of amine) and 50 mL of $CH_2Cl_2$ and 1 mL of DIEA (6.46 mmole) and the mixture was shaken for 5 minutes. After 5 minutes the mixture was washed three times with $CH_2Cl_2$ and then shaken for 30 seconds. To the mixture was then added 0.3 mL (2.1 mmole) of diisopropylcarbodiimide (DIC) and the mixture was then shaken in the dark for 7 hours. After 7 hours the mixture was filtered and washed three times with $CH_2Cl_2$, four times with methanol and five times with $CH_2Cl_2$ in that order. The resin was then placed under pump vacuum for several hours to give 3.1 grams of 11 as a white solid. The amount of resin-bound amine after derivitization was measured by quantitative ninhydrin (0.24 mmole of chloroMpact/g of resin).

EXAMPLE 6

Coupling of NpSSMpact to TentaGel to give NpSSMpact-PEG-PS (12).

This was done following the same procedure as the chloroMpact-PEG-PS (11) synthesis, starting with 3 grams of TentaGel (0.87 mmole) resin 10 and 0.9 grams (2.2 mmole) of NpSSMpact (5) linker and 0.3 mL (2.1 mmole) of DIC to isolate 3.2 grams of 12 as a yellow solid. The amount of disulfide on the resin was determined by a modified Ellman spectrophotometric assay at 490 nm (0.18 mmole of disulfide/g of resin) [This procedure is described in I. Sucholeiki et al., *J. Org. Chem.* (1993)58: 1318].

EXAMPLE 7

Synthesis of benzylmercaptan containing resin (13).

To a peptide synthesis vessel was added 1.0 grams (0.24 mmole) of the chloroMpact-PEG-PS support 11, 7 ml of DMF, 0.5 mL of DIEA (2.87 mmole) and 0.2 mL of benzylmercaptan (1.7 mmole) and the mixture was shaken in the dark for 7 hours. After 7 hours the mixture was washed seven times with DMF, four times with methanol, three times with $CH_2Cl_2$, twice with methanol and then twice with $CH_2Cl_2$ in that order. The resin was then placed under pump vacuum to give 0.98 grams of 13 as a tan solid.

EXAMPLE 8

Synthesis of 4-phenylbenzylmercaptan containing resin (14).

To a peptide synthesis vessel containing 2.3 grams (0.43 mmole) of NpSSMpact-PEG-PS resin 12 was added 15 mL of DMF, 0.25 mL (3.5 mmole) of β-mercaptoethanol and 0.4 mL (2.3 mmole) of diisopropylethylamine and mixture shaken for 2–3 minutes. The red colored mixture was then filtered and the process repeated two more times using the same quantities of BME and DIEA. The resin was then washed five times with DMF, three times with methanol, four times with $CH_2Cl_2$ and then three times with DMF. To the resin was then added 0.3 grams (1.21 mmole) of 4-phenyl benzyl bromide dissolved in 15 mL of DMF and 0.5 mL (2.87 mmole) of DIEA and shaken in the dark for 6.5 hours. After 6.5 hours, the mixture was then filtered and washed five times with DMF, three times with methanol and six times with $CH_2Cl_2$ in that order. The resin was then dried under pump vacuum to give 2.2 grams of 14.

EXAMPLE 9

Synthesis of 4-phenylbenzylthioether resin (16).

To a synthesis vessel containing 1.0 gram (0.29 mmole) of TentaGel resin 10 was shaken with 0.5 mL (2.87 mmole) of diisopropylethylamine dissolved in 15 mL of $CH_2Cl_2$ for one minute. The resin was then filtered and washed three times with $CH_2Cl_2$. To the resin was then added 0.17 grams (0.62 mmole) of thioether 15 dissolved in 15 mL $CH_2Cl_2$ and 0.15 mL (0.95 mmole) of diisopropylcarbodiimide and mixture shaken for 4 hours. (The biphenyl acid 15 was synthesized from 4-phenylbenzyl bromide [P. J. Kocienski et al., *J. Org. Chem.* (1977) 42: 353] and 3-mercaptopropionic acid to give the resulting thioether 15). The mixture was then filtered and washed repeatedly with $CH_2Cl_2$, methanol and then $CH_2Cl_2$, in that order. The resin was placed under vacuum overnight to give 1.0 gram of 16. The amount of resin-bound amine after derivitization was measured by quantitative ninhydrin (0.28 mmole of biphenyl/g of resin).

EXAMPLE 10

General Photochemical Cleavage Procedure For C—S Bond.

To a quartz test tube (15.5×1.5 cm) containing a tiny stir bar was added 0.3 grams (0.05–0.08 mmoles) of thioether (13, 14 or 16) containing resin. To the resin was then added 5 mL of acetonitrile and the mixture cooled to freezing using a dry ice-acetone bath. The frozen solid was then exposed to a pump vacuum and then thawed under closed vacuum. This process was then repeated three more times with the last thawing done under nitrogen atmosphere. The stirred mixture was then irradiated under closed nitrogen atmosphere using a Rayonet photochemical reactor (consisting of sixteen black light phosphor bulbs having a maximum wavelength intensity at 350 nm) for periods of between 2–5 hours. After irradiation, the mixture was filtered through a medium porosity fritted glass funnel and volatile components removed under reduced pressure. The products were analyzed by reverse-phased HPLC, EI and/or FAB mass spectrometry, GC Mass spectrometry and $^1H$ NMR spectroscopy.

The disclosures of all references cited in this specification are incorporated in their entirety by reference.

The invention being thus described, it will be obvious that the same may be varied in many ways. Such variations are not to be regarded as a departure from the spirit and scope of the invention and all such modifications are intended to be included within the scope of the following claims.

What is claimed is:

1. A compound having the following formula:

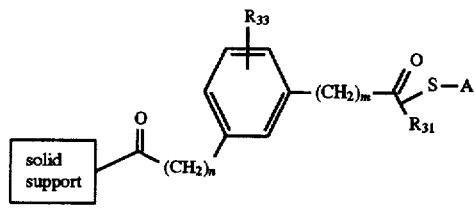

wherein:

A is an organic non-peptide compound $R_{31}$ is selected from the group consisting of $C_{1-4}$ alkyl;

$R_{33}$ is selected from the group consisting of H and up to three $C_{1-4}$ alkoxy substituents;

n is 1 to 10; and m is 0 to 10.

2. The compound of claim 1 wherein $R_{31}$ is $CH_3$ and $R_{33}$ is selected from the group consisting of H, $OCH_3$ and $OCH_2CH_3$.

3. The compound of claim 2 wherein $R_{33}$ is $OCH_3$, n is 1 and m is 0.

* * * * *

UNITED STATES PATENT AND TRADEMARK OFFICE
CERTIFICATE OF CORRECTION

PATENT NO. : 5,693,720
DATED : December 2, 1997
INVENTOR(S) : Sucholeiki, Irving It is certified that error appears in the above-indentified patent and that said Letters Patent is hereby corrected as shown below:

Column 7, lines 62-65: should read--

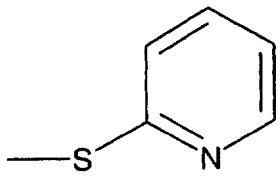

Column 8, lines 30-35: should read --

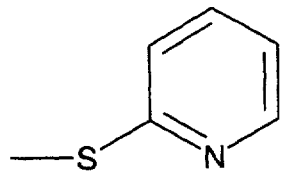

Signed and Sealed this

Twentieth Day of March, 2001

Attest:

NICHOLAS P. GODICI

*Attesting Officer*  *Acting Director of the United States Patent and Trademark Office*